(12) United States Patent
Cao et al.

(10) Patent No.: US 11,730,455 B2
(45) Date of Patent: Aug. 22, 2023

(54) ULTRASOUND PROBE TRANSDUCER TESTING

(71) Applicant: KONINKLIJKE PHILIPS N.V., Eindhoven (NL)

(72) Inventors: Ji Cao, Bothell, WA (US); Patrick Lambert, Bothell, WA (US); Mark Potts, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 598 days.

(21) Appl. No.: 16/758,296

(22) PCT Filed: Oct. 16, 2018

(86) PCT No.: PCT/EP2018/078203
§ 371 (c)(1),
(2) Date: Apr. 22, 2020

(87) PCT Pub. No.: WO2019/081269
PCT Pub. Date: May 2, 2019

(65) Prior Publication Data
US 2020/0253589 A1 Aug. 13, 2020

Related U.S. Application Data

(60) Provisional application No. 62/575,562, filed on Oct. 23, 2017.

(51) Int. Cl.
*A61B 8/00* (2006.01)
*A61B 8/14* (2006.01)

(52) U.S. Cl.
CPC ............... *A61B 8/58* (2013.01); *A61B 8/145* (2013.01)

(58) Field of Classification Search
CPC ... G01R 31/2829; G01S 7/52004; G01N 29/30; G01N 29/4436; G01N 2291/106;
(Continued)

(56) References Cited

U.S. PATENT DOCUMENTS 5,517,994 A * 5/1996 Burke ................ G01S 7/5205
600/443
2004/0213417 A1 * 10/2004 Gessert ............. H04R 29/002
381/66
(Continued)

FOREIGN PATENT DOCUMENTS

EP 1629779 A1 3/2006
EP 3175793 A 6/2017
(Continued)

OTHER PUBLICATIONS

International Search Report and Written Opinion for International Application Serial No. PCT/EP2018/078203, filed Oct. 16, 2018, 12 pages.

*Primary Examiner* — Boniface Ngathi N

(57) ABSTRACT

An ultrasound probe is tested for failure of 5 elements of its array transducer by operating the probe with its lens in contact with the air. The echo signals produced during this mode of operation are beamformed into the usual set of scanlines produced by the probe. The frequency response of 10 each scanline is analyzed and compared with a reference signal of the frequency response of the corresponding scanline of a known good probe of the same type as the probe under test. If a comparison reveals a variance greater than a predetermined 15 deviation, the user is alerted that the probe should be replaced.

13 Claims, 3 Drawing Sheets

(58) Field of Classification Search
CPC .... G01N 2291/104; A61B 8/58; A61B 8/145; A61B 8/06
See application file for complete search history.

(56) References Cited

U.S. PATENT DOCUMENTS

| | | |
|---|---|---|
| 2009/0260443 A1 | 10/2009 | Suita et al. |
| 2014/0126791 A1 | 5/2014 | Iimura et al. |
| 2014/0241115 A1* | 8/2014 | Thattari Kandiyil ........................ G01S 7/52004 367/13 |

FOREIGN PATENT DOCUMENTS

| | | |
|---|---|---|
| JP | 2002159492 A | 6/2002 |
| JP | 2006095291 A | 4/2006 |
| JP | 2013165880 A | 8/2013 |

* cited by examiner

ULTRASOUND PROBE TRANSDUCER TESTING

RELATED APPLICATIONS

This application is the U.S. National Phase application under 35 U.S.C. § 371 of International Application No. PCT/EP2018/078203, filed on Oct. 16, 2018, which claims the benefit of and priority to Provisional Application Ser. No. 62/575,562, filed Oct. 23, 2017. These applications are incorporated by reference herein.

This invention relates to ultrasonic diagnostic imaging systems and, in particular, to systems and methods for testing the operability of transducer arrays in ultrasound probes.

Ultrasonic diagnostic imaging systems are designed to operate with different kinds of ultrasound probes designed for specific imaging procedures. Modern imaging probes use array transducers to send and receive ultrasound, with groups of elements operated together. Linear array probes use a subset of the array of elements as the active aperture for each scanline, which is progressively shifted across the array to scan the full complement of scanlines, a process known as "tractor-treading." Phased array probes operate all of the elements for both transmission and reception of each differently steered scanline. Each transducer element is electrically connected to a microbeamformer in the probe, which in turn is connected by a cable to a beamformer in the system mainframe, or directly by the cable to the system beamformer. These electrical connections can fail over time, and the affected element will then no longer contribute to the beam formation for which it is programmed to be used. While the failure of a single transducer element will generally not render a probe inoperable for imaging, it can have an effect on image quality which may be discerned by a user grown accustomed to a certain level of performance by the probe. Thus it is desirable to be able to test a probe for failed transducer elements in the event of a falloff in image quality. It is known to test array probes for failed elements on an element-by-element basis as described in U.S. Pat. No. 5,517,994 (Burke et al.) While such testing can locate a defective array element, it would be preferable to approach the problem from an image quality perspective, as that is generally how the user perceives the problem. Furthermore, testing individual elements can be problematic in the case of two dimensional array transducers with thousands of elements with the connections to beamformer channels made at the microbeamformer level in the probe. Accordingly it would be desirable to diagnose and identify problems with failed transducer elements by analyzing their effects on image quality.

In accordance with the principles of the present invention, an ultrasound system and test method are described for diagnosing transducer probe performance problems from the perspective of image quality. Rather than analyzing connections of individual transducer elements, the inventive system and method operate on beamformed signals from the probe. The beamformed signal response is compared with a probe response reference signal and variations between the beamformed signal and the reference in excess of a level known to affect image quality are used as indicators of probe failure. For example, the variations can be in the frequency response of one or more scanlines across the aperture of the array. In certain aspects, the systems and methods can specifically test the performance of a transducer per imaging mode, e.g., for its operation in 2D, color Doppler, PW, CW, and 3D. The per mode analysis for the transducers is one of the merits from post-beamformed data analysis for testing.

Figure 1:
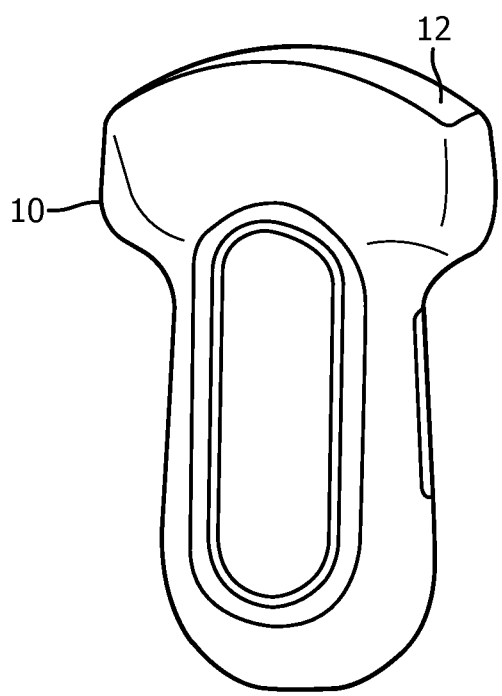
FIG. 1 is an illustration of an ultrasound array transducer probe.

Referring first to FIG. 1, an ultrasound probe 10 is shown. In use, the probe is held by the bottom (handle) portion and the lens 12 on the top surface is pressed against the body of the subject during scanning. Behind the lens is a transducer array, part of what is known as the transducer stack assembly, which transmits ultrasound waves into the subject and receives echoes therefrom for image formation. The probe 10 is connected to a mainframe ultrasound system either wirelessly or by a cable extending from the bottom of the probe (not shown).

Figure 2:
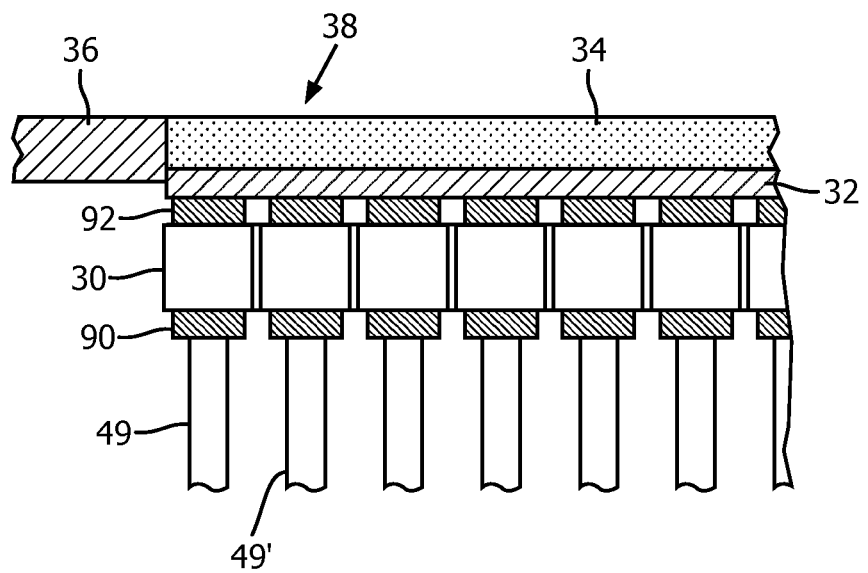
FIG. 2 is a cross-sectional view of the construction of a typical array transducer in an ultrasound probe.

FIG. 2 is a cross-sectional view of a typical transducer stack assembly. An acoustic lens 34 of RTV rubber has its outer patient-contacting surface flush with the probe case 36. The acoustic lens covers one or more acoustic matching layers 32 which match the acoustic impedance of the transducer to that of the acoustic lens and tissue. The matching layer 32 overlays the transducer elements 30 which have electrodes 90, 92 plated on their outer and inner surfaces. The lower electrodes 90 are generally signal electrodes and the upper electrodes 92 are return electrodes. A number of conductors 49, 49' extend from the transducer electrodes and are joined to individual conductors of a probe cable when used. The volume behind the transducer 30 and shown occupied by the conductors 49, 49' is filled with acoustic damping material which damps acoustic energy emanating from the back of the transducer array.

Figure 3:
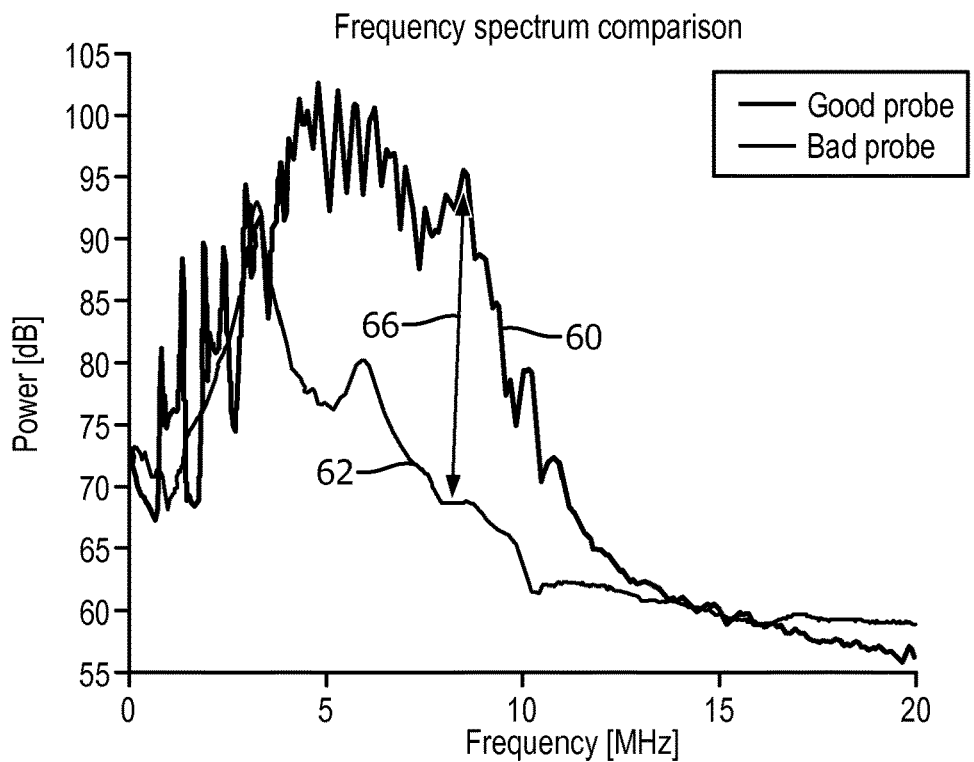
FIG. 3 is a graphical comparison of the frequency response of a probe scanline with a reference response for that probe.

A transducer failure mode which can be detected by an implementation of the present invention is a conductor 49 coming loose from its electrode 90, 92, rendering the affected transducer element 30 unable to transmit or receive ultrasound signals. The transducer conductors are coupled to channels of a beamformer which actuates a group of elements to transmit properly steered and focused ultrasound beams, and delays and sums signals received by a group of elements to form coherent echo signals from along steered and focused beam directions. For example, a transducer array of 192 transducer element may have its received signals processed in sub-aperture groups by a beamformer to produce 128 scanlines of coherent echo signals. In accordance with the principles of the present invention, the power and frequency characteristics of each scanline are analyzed and compared to reference characteristics for scanlines of the particular probe type. FIG. 3, for example, illustrates a frequency spectrum 62 for one scanline of a tested probe in comparison with a reference spectrum 60 which is typical for the same scanline of the same probe type. In this example it is seen that the frequency spectra track each other at low frequencies up to about 3 MHz, after which the spectrum 62 of the tested probe falls off rapidly in comparison to the reference spectrum 60. As the arrow 66 indicates, there is over 20 dB difference in the frequency response of the tested probe at higher frequencies in comparison with the expected reference spectrum. Since users can see differences in probe performance as small as 3 dB, the tested probe in this example is judged to be defective and should be replaced.

Figure 4:
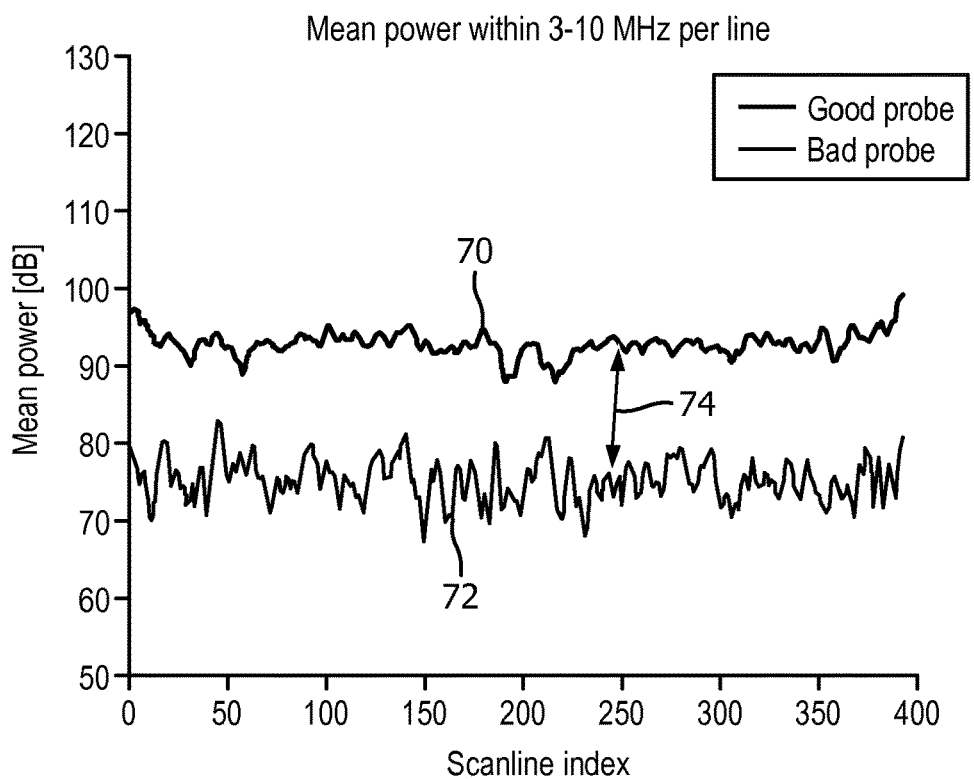
FIG. 4 is a graphical comparison of the response of each scanline of a probe with a reference response for each scanline.

FIG. 4 illustrates another probe test of the present invention. In this example the frequency response of each scanline produced by a beamformer from a probe is measured as shown in FIG. 3, and the mean power over the 3-10 MHz portion of each spectrum is calculated. These mean power values for the scanlines of the test probe are plotted to form a plot 72 in FIG. 4. Above the plot 72 of the test probe values, mean power values of reference scanlines for the probe type are plotted as shown at 70. As indicated by the arrow 74, the scanline response of the test probe is consistently 5-10 dB or more below the expected scanline response 70 for that type of probe. Again, the probe is judged to be defective and should be replaced.

Figure 5:
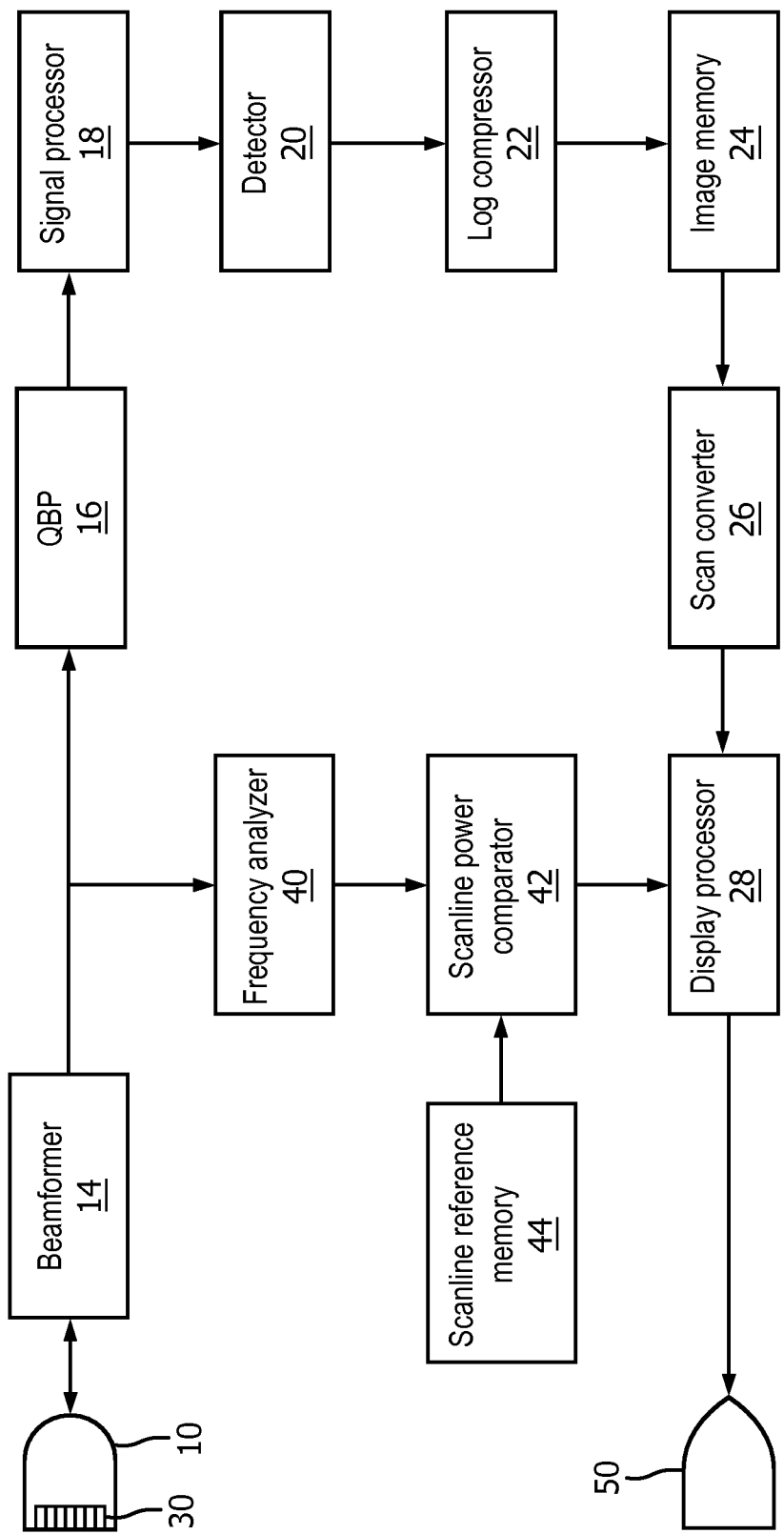
FIG. 5 illustrates in block diagram form an ultrasound system constructed in accordance with the principles of the present invention.

FIG. 5 illustrates in block diagram form an ultrasound system constructed in accordance with the principles of the present invention. A transducer array 30 is provided in an ultrasound probe 10 for transmitting ultrasonic waves and receiving ultrasonic echo signal information. The transducer array 30 may be a one- or two-dimensional array of transducer elements capable of scanning in two or three dimensions, for instance, in both elevation (in 3D) and azimuth. A two-dimensional array probe will include a microbeamformer coupled to the array elements which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer or the transducer elements are coupled by a probe cable to a beamformer 14. The transmission of ultrasonic beams from the transducer array 30 under control of a microbeamformer when so equipped, or directly if there is no microbeamformer, is directed by a transmitter in the beamformer, which receives input from the user's operation of a user interface or control panel of the ultrasound system (not shown). Among the transmit characteristics controlled by the transmitter are the frequency, amplitude, phase, and polarity of transmit waveforms. Beams formed in the direction of pulse transmission may be steered straight ahead from (orthogonal to) the transducer array which is typical of a linear array probe, or at different angles to scan a wider field of view as is typical of a phased array probe.

The echoes received by a group of transducer elements, a sub-aperture of the array in the case of a linear array or the entire array in the case of a phased array, are beamformed in the beamformer 14 by appropriately delaying them in accordance with the desired beam steering and focusing, and then combining them. Analog beamformers are known, but modern ultrasound systems perform beamforming in the digital domain by converting received echo signals to digital signal samples prior to beam formation. The partially beamformed signals produced by a microbeamformer are digitized and combined into fully beamformed coherent echo signals by the beamformer. A scanline produced by a digital beamformer thus comprises a sequence of coherent echo signal samples from the shallowest to the deepest depth of the scan.

The coherent echo signals are coupled to a quadrature bandpass filter (QBP) 16. The QBP performs three functions: band limiting the RF echo signal data, producing in-phase and quadrature pairs (I and Q) of echo signal data, and decimating the digital sample rate. The QBP comprises two separate filters, one producing in-phase samples and the other producing quadrature samples, with each filter being formed by a plurality of multiplier-accumulators (MACs) implementing an FIR filter. The quadrature signal samples undergo signal processing by a signal processor 18, which includes filtering by a digital filter and speckle reduction as by spatial or frequency compounding. The signal processor can also shift the frequency band to a lower or baseband frequency range, as can the QBP. The digital filter of the signal processor 18 can be a filter of the type disclosed in U.S. Pat. No. 5,833,613 (Averkiou et al.), for example.

The beamformed and processed coherent echo signals are coupled to a detector 20. For B mode (tissue structure) imaging, the detector performs amplitude detection of the echo signals by processing the I, Q samples in accordance with the algorithm $(I^2+Q^2)^{1/2}$. For Doppler (flow and motion) imaging, the detector stores ensembles of echo signals from discrete points in an image field which are then used to estimate the Doppler shift at points in the image with a fast Fourier transform (FFT) processor. For a color Doppler image, the estimated Doppler flow values at each point in a blood vessel are wall filtered and converted to color values using a look-up table. B mode echo signals then undergo log compression in a log compressor 22 which converts their linearly disposed intensity values to logarithmically disposed intensity values by use of a look-up table, thereby producing a more diagnostic range of grayscale intensity values of tissue. The Doppler and tissue signals, now in a form for use as pixels of an image, are stored in an image memory 24.

Both B mode image signals and the Doppler flow or motion values are coupled to a scan converter 26 which converts the B mode and Doppler scanlines from their acquired R-θ coordinates to Cartesian (x,y) coordinates for display in a desired display format, e.g., a rectilinear display format or a sector display format. Either the B mode image or the Doppler image may be displayed alone, or the two shown together in anatomical registration in which the color Doppler overlay shows the blood flow in tissue and vessel structure in the B mode image. The ultrasound images produced by the scan converter 26 are coupled to a display processor 28 which produces signals suitable for producing a display of the ultrasound image on an image display 50.

When a probe is to be tested for failed transducer elements in accordance with the present invention, the probe is operated while not in contact with a subject. That is, the lens 34 of the probe is facing air and the transmitted ultrasound waves are reflected back to the transducer elements 30 from the air-lens interface 38 as shown in FIG. 2. The reflected signals are received by the transducer elements 30 and coupled to the beamformer 14, which beamforms the signals into coherent echo signals along receive scanline directions. The echo signals of each scanline are applied to a frequency analyzer 40 which, in a preferred implementation, comprises a processor executing a fast Fourier transform algorithm, the same type of processing used for Doppler processing as mentioned above. As is well known, Fourier transformation will convert a sequence of amplitude signal samples to the frequency domain, and FFT algorithms have been in widespread use for amplitude to frequency conversion since the FFT algorithm was published by Cooley and Tukey in 1965. The frequency analyzer 40 thus produces a frequency spectrum as shown at 62 in FIG. 3. A scanline reference memory stores a reference frequency spectrum 60 acquired from testing a known good probe of the same type as probe 10. The frequency spectra produced by the frequency analyzer 40 and the scanline reference memory 44 are coupled to a scanline power comparator 42, which compares the two spectra over their range of frequencies, such as the 3-10 MHz range of the spectra in FIG. 2. If the frequency-by-frequency comparison shows that the spectra are continually within a desired range of each other, e.g., 3 dB, then the comparator applies a "good" signal to the display processor 28, and this test result is displayed on the display screen 50. If the comparison shows that the spectra divergences exceed the desired range, as is the case of the two spectra of FIG. 3 above for the 3-10 MHz range, then the comparator causes a "defective" signal to be displayed on the display. This test is repeated for each scanline, retrieving a corresponding scanline reference spectrum from the memory 44 for comparison each time, until each scanline produced from the probe has been analyzed and tested.

The test methodology of FIG. 4 may additionally or alternatively be employed for the test. In such case, a reference plot 70 of the mean power of the scanlines of a known good probe over a predetermined frequency range, such as the 3-10 MHz range used in FIG. 4, is stored in the scanline reference memory 44 and retrieved by the scanline power comparator for comparison. The mean power value of each scanline frequency spectrum from the test probe is calculated over the same predetermined frequency range by the scanline power comparator, producing a mean power value for each scanline which may be plotted for all the scanlines as shown by plot 72. The scanline power comparator 42 then compares the reference and test probe plots and, if they diverge for any scanline by more than a predetermined amount such as 3 dB, then the comparator sends a "defective" test result for display on the display 50. If the plots are within the desired range of each other, a "good" result is displayed to the user.

It should be noted that an ultrasound system suitable for use in an implementation of the present invention, and in particular the component structure of the ultrasound system of FIG. 5, may be implemented in hardware, software or a combination thereof. The various embodiments and/or components of an ultrasound system, for example, the frequency analyzer 40 and the scanline power comparator 42, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system or the data network for importing high and low frequency images. The computer or processor may also include a memory. The memory devices such as the image memory 24 and the scanline reference memory 44, may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and transmission of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as an FFT algorithm module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasonic diagnostic imaging system which tests transducer probes for image quality deficiency comprising:
    an ultrasound probe comprising an array of transducer elements adapted to acquire ultrasonic echo signals;
    a beamformer coupled to the array of transducer elements and adapted to form beamformed echo signals of scanlines from a plurality of acquired echo signals;
    a frequency analyzer coupled to receive beamformed echo signals and adapted to produce a signal indicating the frequency response of beamformed echo signals;
    a memory adapted to store reference signals of the frequency response of beamformed signals;
    a comparator adapted to compare the frequency response produced by the frequency analyzer with a reference signal and to produce an output signal identifying a defective probe when the comparison indicates an unacceptable difference between the frequency response and the reference signal; and
    a display coupled to receive the output signal from the comparator and adapted to display an indication of the defective probe,
    wherein the frequency analyzer further comprises a fast Fourier transform (FFT) algorithm adapted to produce a power versus frequency response of scanline echo signals, and
    wherein the memory is further adapted to store reference signals of the power versus frequency response of scanlines of the ultrasound probe.

2. The ultrasonic diagnostic imaging system of claim 1, wherein the ultrasound probe further comprises a lens covering the array of transducer elements, and
    wherein the beamformer is further adapted to form the beamformed echo signals of scanlines when the lens is in contact with air.

3. The ultrasonic diagnostic imaging system of claim 1, wherein the ultrasound probe is a linear array probe.

4. The ultrasonic diagnostic imaging system of claim 1, wherein the ultrasound probe is a phased array probe.

5. The ultrasonic diagnostic imaging system of claim 1, wherein the comparator is further adapted to compare the power versus frequency response of scanlines of the ultrasound probe with reference signals of the power versus frequency response of scanlines stored in the memory.

6. The ultrasonic diagnostic imaging system of claim 5, wherein the display is further adapted to produce a display of the power versus frequency response of a scanline of the ultrasound probe with a reference signal of the power versus frequency response of a scanline of the ultrasound probe.

7. The ultrasonic diagnostic imaging system of claim 6, wherein the memory is further adapted to store reference signals of the power versus frequency response of scanlines of a known good ultrasound probe of the same type as the ultrasound probe.

8. The ultrasonic diagnostic imaging system of claim 1, wherein the comparator is further adapted to calculate the mean power of the power versus frequency response of scanline echo signals produced by the frequency analyzer.

9. The ultrasonic diagnostic imaging system of claim 8, wherein the memory is further adapted to store reference signals of the mean power of scanline signals of the ultrasound probe.

10. The ultrasonic diagnostic imaging system of claim 9, wherein the comparator is further adapted to compare mean power values of the power versus frequency response of scanline echo signals produced by the probe with reference mean power values.

11. The ultrasonic diagnostic imaging system of claim 10, wherein the display is further adapted to produce a display of the mean power values of scanlines of the probe with reference signals stored in the memory of mean power values of a probe.

12. The ultrasonic diagnostic imaging system of claim 11, wherein the display is further adapted to produce a display of a plot of the mean power values of scanlines of the probe with a plot of reference signal mean power values of a probe stored in the memory.

13. The ultrasonic diagnostic imaging system of claim 11, wherein the memory is further adapted to store reference signals of mean power values of a known good probe of the same type as the ultrasound probe.

\* \* \* \* \*